United States Patent
Lin

(10) Patent No.: US 8,318,152 B2
(45) Date of Patent: Nov. 27, 2012

(54) EFFECTS OF PROBIOTICS ON HUMANS AND ANIMALS UNDER ENVIRONMENTAL OR BIOLOGICAL CHANGES

(75) Inventor: Jhy-Jhu Lin, Potomac, MD (US)

(73) Assignee: Imagilin Technology, LLC, Frederick, MD (US)

( * ) Notice: Subject to any disclaimer, the term of this patent is extended or adjusted under 35 U.S.C. 154(b) by 525 days.

(21) Appl. No.: 12/386,285

(22) Filed: Apr. 16, 2009

(65) Prior Publication Data

US 2009/0263366 A1     Oct. 22, 2009

Related U.S. Application Data

(60) Provisional application No. 61/124,424, filed on Apr. 16, 2008.

(51) Int. Cl.
*A01N 63/00* (2006.01)
*C12N 5/04* (2006.01)

(52) U.S. Cl. ............... 424/93.45; 424/827; 435/411; 435/822

(58) Field of Classification Search ............... None
See application file for complete search history.

(56) References Cited

U.S. PATENT DOCUMENTS

| 5,501,857 A * | 3/1996 | Zimmer | 424/438 |
| 2004/0175460 A1* | 9/2004 | Zenovich | 426/42 |
| 2004/0223956 A1* | 11/2004 | Naidu et al. | 424/93.45 |

FOREIGN PATENT DOCUMENTS

WO     2004028460     * 4/2004

* cited by examiner

*Primary Examiner* — Debbie K Ware
(74) *Attorney, Agent, or Firm* — Stein McEwan, LLP

(57) ABSTRACT

An exemplary embodiment providing one or more improvements includes probiotic compositions comprising probiotic microorganisms with dried vegetable, fruit, cereal, or herb powder. Feeding human or animals either having biological or environmental changes with probiotic compositions has a positive effect in relieving the changes. Positive effects has been demonstrated in humans, dogs, and fish.

4 Claims, No Drawings

EFFECTS OF PROBIOTICS ON HUMANS AND ANIMALS UNDER ENVIRONMENTAL OR BIOLOGICAL CHANGES

CROSS-REFERENCES TO RELATED APPLICATIONS

This is a continuation-in-part application to provisional application No. 61/124,424, filed Apr. 16, 2008.

STATEMENT REGARDING FEDERALLY SPONSORED RESEARCH OR DEVELOPMENT

Not Applicable.

THE NAMES OF THE PARTIES TO A JOINT RESEARCH AGREEMENT

Not Applicable.

REFERENCE TO A "SEQUENCE LISTING," A TABLE, OR A COMPUTER PROGRAM LISTING APPENDIX

Not Applicable.

BACKGROUND

Probiotics are beneficial microorganisms naturally existing in gastrointestinal (GI) tracts of humans and animals. Probiotics are described to have health benefits when administered the right amounts of live microorganisms into humans and animals. Probiotics are widely applied as nutritional supplements in animals and humans. For example, yeast is used as a nutrient supplement for livestock, and yogurt with lactic acid bacteria *Lactobacillus* and/or *Bifidobacterium* is commonly used. No toxic effects are described when administered probiotics as nutrition supplements into humans and animals. In order to have the maximum effects of probiotics on animals and humans, one has to administrate live bacteria to reach gastrointestinal tracts for multiplication (Kailasapatha and Chin 2000). *Lactobacillus* spp and *Bifidobacterium* spp are two most commonly probiotics described in scientific literature and in commercial products. Both *Lactobacillus* spp and *Bifidobacterium* spp are facultative anaerobic bacteria. Most species (or strains) of *Lactobacillus* and *Bifidobacterium* are sensitive to the exposure of oxygen (Gomes et al, 1995: Talwalkar and Kailasapathy, 2004) and high temperature. It is difficult to maintain the viability of *Lactobacillus* and *Bifidobacterium* at room temperature under consistent open and closure operations. Therefore, variable results are often described, especially for commercially available products that are required to have long term storage and shipping in various temperature (Tuomola et al, 2001).

Vegetables and fruits are the main sources of fibers, vitamins, natural antioxidants and minerals for humans and animals. For examples, tomato and cabbage were described as the natural source of vitamin C (Clayton and Borden, 1942). More important, the safety of vegetables and fruits has been well accepted. Recently, natural berries like Acerola that is described to be rich in ascorbic acid and polyphenols. The high content in vitamin C (695 a 4827 mg/100 g) make Acelora as the preferred choice of natural vitamin C (Mezadri et al, 2006). In addition, recent study in rats demonstrated that Acelora is safe to be as food supplement for human consumption (Hanamura and Aoki, 2008). The combination of probiotics with fresh vegetables or fruits will offer benefits from probiotics and fresh vegetables or fruits. However, fresh vegetables and fresh fruits are the natural nutritional sources for microorganisms to multiply. The replication of microorganisms in fresh vegetables and fruits not only changes the nutritional compositions of vegetables or fruits but also creates toxic compounds which either are secreted from microorganisms or generated as the side products from the replication of microorganisms or decomposition of vegetables or fruits. Whenever probiotics start to be active, it becomes difficult to keep them alive for long term storage, especially at room temperature.

Research scientists and commercial companies have developed different dried process to preserve the vegetables and fruits. The main challenges of dried vegetables or fruits are to maintain nutrition and flavors of vegetables and fruits. It is critical during the drying process to maintain the minerals, vitamins, carbohydrates, proteins, and antioxidants of vegetables or fruits as much as possible, especially for dried vegetable or fruit powders. In addition, during the drying process and storage, the loss of nutrition and flavors of dried vegetables or fruit powders has to be minimal to have the nutritional benefits as fresh vegetables and fruits.

It is well known that when one mixed probiotics with minerals or other animal feed additives, the viability of the probiotics decreased significantly. Single l s encapsulation of the mixture of probiotics with vitamin and mineral supplements within a gelatin capsule resulted in the loss of more than 99.79% of viability of the probiotics (Zimmer, 1996, U.S. Pat. No. 5,501,857). This creates a major challenge: to add probiotics to dried vegetable or fruit powders which required keeping the minerals, vitamins, antioxidants and flavors of the powders while maintaining the viability of the probiotics.

Humans and animals are venerable to become ill under environmental changes, such as separation from family, travel, stay in hotel or boarding facilities, or temperature or by biological changes such as aging, diet changes, pathogens or parasites infection, or antibiotic treatment. Such environmental changes often show an increase in the release of hormones. The most important of these hormones is cortisol from the adrenal cortex. Cortisol causes a suppression of the inflammatory response (Roberts et al. 2006). Prolonged increased levels of cortisol cause a decreased ability to mount an immune response (Roberts et al. 2006). A suppressed immune system impacts the host in many ways, for example, there is a weakened ability to engulf invading bacteria. Elevated blood cortisol affects the fluidity of macrophage membranes; macrophage ability to kill ingested pathogens is reduced when the immune system is suppressed (Mayo Clinic 2006). Medical doctors and veterinarians often treat gastrointestinal (GI) diseases with weeks of antibiotic or steroid therapy. Prolonged use of broad-spectrum antimicrobials, however, can disrupt the populations of beneficial microorganisms in human and animal GI tracts, and cause side effects of digestive disorders. Application of steroids in human and animal often caused disruption of natural hormones, cardiovascular disease, liver disease, and skin disease. Usage of probiotics to negate impacts changes caused by environmental or biological changes of humans or animals decreases the reliance medical doctors and veterinarians have on antibiotics and steroids.

The foregoing examples of the related art and limitations related therewith are intended to be illustrative and not exclusive. Other limitations of the related art will become apparent to those of skill in the art upon a reading of the specification.

BRIEF SUMMARY

The following embodiments and aspects thereof are described and illustrated in conjunction with systems, tool and methods which are meant to be exemplary and illustrative, not limiting in scope. In various embodiments, one or more of the above-described problems have been reduced or eliminated, while other embodiments are directed to other improvements.

Embodiments include compositions comprised of probiotics and a dried plant powder. Embodiments include probiotic microorganisms such as *Pediococcus, Bifidobacterium, Bacteroides, Propionibacterium, Streptococcus, Enterococcus, Lactococcus, Lactobacillus*, and *Saccharomyces*. Embodiments include dried plant powders from vegetables, fruits, cereals and herbs. In embodiments compositions are encapsulated in gelatin capsules.

Embodiments include the process of ameliorating effects caused by environmental or biological changes in human or animals comprising the step of: feeding the human or animal in need of such amelioration an encapsulated probiotic composition comprising a viable encapsulated probiotic microbe. Environmental change is defined as stay in boarding facilities, travel, temperature changes, new and or detrimental changes in the immediate human or animal area or scene. Biological change is defined as aging of humans and animals, infection by pathogens or parasites, chronic physiological changes, and changes in established bodily functions.

Embodiments include the process of ameliorating effects caused by environmental or biological changes in human or animals comprising the step: feeding the human or animal in need of amelioration an encapsulated probiotic composition comprising: a probiotic microorganism and a dried plant powder.

In addition to the exemplary aspects and embodiments described above, further aspects and embodiments will become apparent by reference to the drawings and by study of the following descriptions.

BRIEF DESCRIPTION OF THE DRAWINGS

Not applicable.

DETAILED DESCRIPTION

*Pediococcus acidilactici* fermentation cultures were blended with tomato spray dried powders at the weight ratio of 1:4. Encapsulated 500 mg mixtures of *P. acidilactici* and dried tomato powders into a size O gelatin capsules by manual capsule filling apparatus or automatic capsule filling machine. The gelatin capsules were stored at room temperature. Capsules were stored at room temperature and were taken from day 0, 1, 3 and 6 month after stored at room temperature. After separated the capsules, 1 gm of the mixtures of *P. acidilactici* and tomato dried powders were resuspended up to 10 ml sterilized saline buffer. A series of standard dilution were performed, and 100 ul of $10^{-7}$ or $10^{-8}$ dilutions were sprayed onto MRS (de Man, Rogosa and Sharpe) agar plates. The plates were incubated at 45° C. until colonies were observed for quantitative analysis. The bacterial viability is shown in Table 1.

TABLE 1

Stability of encapsulation of *Pediococcus acidilactici* fermentation cultures with tomato dried powders in a gelatin capsule at room temperature

| Time after Manufacture, Months | Number of bacteria CFU/gm | % of survival |
| --- | --- | --- |
| 0 | $2.0 \times 10^{10}$ | 100 |
| 1 | $1.92 \times 10^{10}$ | 96 |
| 3 | $1.94 \times 10^{10}$ | 94 |
| 6 | $1.76 \times 10^{10}$ | 88 |

Table 1 shows that a culture of probiotic microorganisms blended with spray dried tomato powder retains substantial viability for at least six months.

Clients with digestive disorders were volunteers from China, Taiwan and USA, and referred by the local clinics to take NutriTot™, a probiotic composition comprising *P. acidilactici* fermentation cultures in dried vegetable powders such as tomato, carrot, sweet potato, cabbage, spinach or broccoli or fruit powders such as lemon, peach, strawberry, or apple in a gelatin capsule. Administration of NutriTot™: Children<10 years old, half capsule per day; Adult and Children>10 years old, 1 capsule per day Double amounts of NutriTot™ when the symptoms are moderate severe to severe or severe. The results are shown in Table 2.

TABLE 2

Effects of *P. acidilactici* fermentation cultures in dried vegetable powders or fruit powders on human with digestive disorders

| AGE (yrs old) | WEIGHT (Kg) | SEX | CONDITIONS PRIOR TO FEEDING PROBIOTICS .D, O, V, C, F, LA.[1] (Severe: ++++, Moderate to Severe: +++, Moderate: ++, Mild: +, Normal: 0) | TREATMENT (DAYS) | EFFECTS OF TREATMENT (Excellent: ++++, Very Good: +++, Good: ++ Slight Improvement: + No effects: 0)[2] | COMMENTS |
| --- | --- | --- | --- | --- | --- | --- |
| 74 | 44 | F | +++ LA, O | 14 | +++++ | Appetite becomes normal in two days |
| 6 | 20 | M | +++ LA | 14 | +++++ | Appetite becomes normal in two days |
| 75 | 52 | M | ++++ C, LA | 21 | +++++ | Appetite becomes normal in two days, Improved constipation started at week 2 |

TABLE 2-continued

Effects of *P. acidilactici* fermentation cultures in dried vegetable powders or fruit powders on human with digestive disorders

| AGE (yrs old) | WEIGHT (Kg) | SEX | CONDITIONS PRIOR TO FEEDING PROBIOTICS .D, O, V, C, F, LA.[1] (Severe: ++++, Moderate to Severe: +++, Moderate: ++, Mild: +, Normal: 0) | TREATMENT (DAYS) | EFFECTS OF TREATMENT (Excellent: +++++, Very Good: ++++, Good: +++ Slight Improvement: + No effects: 0)[2] | COMMENTS |
|---|---|---|---|---|---|---|
| 65 | 60 | M | ++++ C | 14 | +++++ | Normal bowel movement in 3 days, no more constipation |
| 74 | 66 | M | +++ C | 3 | +++++ | No more constipation |
| 30 | 55 | F | ++++ D | 14 | +++++ | Stop diarrhea in two days, stool showed as banana shape |
| 23 | 50 | F | ++++ D | 2 | +++++ | Diarrhea stop |
| 41 | 75 | M | ++++ O, F, LA | 14 | ++++ | Increase appetite in first week, decrease Flatulence in second week |
| 19 | 65 | M | +++ D | 5 | +++++ | Stop diarrhea |
| 39 | 52 | F | +++ V | 2 | +++++ | Stop vomiting |
| 84 | 84 | M | ++++ C | 30 | +++++ | Improved constipation in first week |
| 7 | 20 | M | +++++ LA | 3 | +++++ | Appetite fully recovered in two days |
| 55 | 158 | F | ++++ D | 180 | +++++ | Stop diarrhea |
| 68 | 174 | M | ++ C | 180 | +++++ | Normal bowel movement, energetic. |

[1]D: Diarrhea, O: bad mouth or body odor, V: Vomiting, C: Constipation, F: Flatulence, LA: Loss of Appetite
[2]Symptoms improvement: Excellent: <2 days, Very Good: between 2 days and 4 days, Good: between 5 days and 14 days, Slight Improvement: between 15 days and 30 days No Improvement: >1 month.

Table 2 shows the beneficial effect on human with biological changes in digestive conditions of feeding with probiotics with dried vegetative powder or dried fruit powder. The beneficial effects often observed within a week or less like two days after NutriTot applications Dogs experience digestive disorders and/or discomforts when kept in boarding facilities for a variety of reasons: the dogs must sleep in a new places, their diet may have changed, they are exposed to other dogs (many of which are barking very loudly), and they do not see the people they normally see every day. These digestive disorders and/or discomfort result from either fear or anxiety (Casey 2002). Fear is defined as an emotional response to a potentially dangerous stimulus, whereas anxiety is the emotional response to a stimulus that predicts a potentially dangerous or unpredictable environment (Casey 2002). Thus, anxiety is the anticipation of harm, whether real or imaginary (Frank et al. 2006).

Two veterinary hospitals in Maryland participated in the study of probiotics on dogs staying the boarding facility. A clinic in Frederick participated from December 2007 through February 2008. A clinic in Baltimore participated from January through March 2008. One hundred fifty-four dogs participated in the study, 83 dogs were in the treatment group, and 71 dogs were in the untreated group, which served as a control. Canines in the test group were fed one capsule of probiotics once a day if less than 50 lbs, two capsules if weighing 50 lbs or more; technicians administering probiotics orally to study participants wrote their initials on study forms indicating the animal had received their daily dosage. Each capsule of probiotics contained an estimated colony forming units (CFU) of *Pediococcus acidilactici* and *Saccharomyces boulardii* from fermented culture.

Veterinary records of all study participants were reviewed for health history and past medications, to track for any potential underlying causes of diarrhea in study participants (i.e. history of frequent diarrhea, usage of antibiotics). Study forms to record each dog's information were used to collect the results.

Differences between treated and untreated group's stool consistency were recorded for all dogs entering the study after the study form was updated. Because of low incidence of diarrhea in study participants, GID scoring, as described below, was used as an alternative measure of intestinal distress. Dogs received one GID score for each bowel movement that was analyzed. A single digit score was made for each stool sample that was analyzed, and scores were recorded on study forms by veterinary staff and described as the followings: normal stool, a GID score of '1,' soft/unformed stool, a GID score of '2, and diarrhea, a GID score of '3'. Higher percentages indicate greater incidence of diarrhea and soft/unformed stool. Values illustrated above were determined by the following formula: (total GID score/total bowel movements)×100=% affected bowel movements. The results are shown in Table 3.

TABLE 3

Effects of probiotics on the dogs staying in boarding facility.

| Parameter | Untreated | Treated | p value (t test) |
|---|---|---|---|
| Number of dogs | 71 | 83 | |
| Total bowel movements | 132 | 233 | |
| GID score | 96 | 29 | |
| Soft stool† | 36 | 7 | <0.0001 |

TABLE 3-continued

Effects of probiotics on the dogs staying in boarding facility.

| Parameter | Untreated | Treated | p value (t test) |
|---|---|---|---|
| Diarrhea† | 7 | 5 | 0.1 |
| Vomiting† | 1 | 0 | 0.18 |

†Data is the incidence of parameter.

Table 3 shows the beneficial effect of probiotics on bowel movements in dogs under the environmental changes of confinement in a boarding facility. A greater incidence of diarrhea and soft stool in boarded untreated dogs than treated dogs.

When fish are transported from a fish breeder to a delivery site they are confined within a plastic bag consisting of water and oxygen, many instances for more than twenty four hours. During transport, the water in these closed containers may become oxygen-depleted, and may accumulate excessive carbon dioxide and consequently undergo a reduction in pH (Cole 1999). Metabolic activity may also lead to elevated ammonia levels in the water, which can be damaging to fish health, or become lethal in extreme cases (Cole 1999).

Disease is a major problem for the fish farming industry (Gram et al. 2003). Although vaccines to fish pathogens are being developed and marketed, they generally cannot be used as a universal disease control measure in aquaculture (Gram et al. 2003). Juvenile fish are not fully immunocompetent and do not always respond to vaccination (Gram et al. 2003).

The goldfish (*Carassius auratus*) belongs to a class of fish called teleost which literally means bony fish. In a study by Ahilan et al. in 2004 qualitative analysis of gut flora of juvenile goldfish was conducted and the presumptively identified microbes were *Micrococcaceae, Arthrobacter, Lactobacillus, Bacillus, Vibrio, Pseudomonas, Acinelobacter, Enterobacteriaceae* and *Alcaligenes*. We apply *Pediococcus acidilactici* to determine the extent to which probiotics influence goldfish under induced physical and/or biological changes. Goldfish were chosen for this study due to the number of mortalities that occur during their handling process, and their vulnerability to infectious diseases along with the ease in obtaining a large number for the study along with the popularity of the fish.

Goldfish (*Carassius auratus*) were obtained from a pet distributor. The fish were fed the probiotic supplemented diet for three days. On the fourth day fecal samples was collected. The physical change was induced by placing the fish in a closed plastic container with water and oxygen for three hours. The fish were continuously fed for two weeks with or without the probiotic supplemented feed. During the two week period the survival rate was observed. For the treatment group, the feed composed of ground up fish feed (Omega One marine pellets, Sitka, Ak.), alginic acid (Acros Organics, N.J.), and 0.1% of the lyophilized probiotic by total weight of the feed mixture. A minimal amount of water was added to the mixture to homogenize. The mixture was then extruded through an empty syringe to obtain thin, long strands of feed. The strands were washed in 0.25M $CaCl_2$, followed by a rinse with de-ionized water. The feed was then cut into appropriate sizes to allow for fish intake. The amount of probiotic in the feed once fully processed corresponds to approximately $1.7 \times 10^8$ cfu/gram of feed. The feed for the control group was processed similarly with the exclusion of the probiotics. Table 4 shows the results.

TABLE 4

Effects of *Pediococcus acidilactici* on mortality of gold fish treated with environmental changes.

| Treatment | Total numbers of gold fish | Number of gold fish dies after physical changes | % of mortality |
|---|---|---|---|
| Control | 21 | 10 | 47.6% |
| *P. acidilactici* | 21 | 4 | 19.0% |

Table 4 shows the effect of probiotics on mortality in fish which went through the environmental changes of confinement, crowding, and elevated temperature.

Goldfish infected by *Ichthypothirius multifilis* were obtained from a pet shop. Using the same conditions as in Table 4, the fish were fed the probiotic supplemented diet for three days. On the fourth day fecal sample was collected. The physical change was induced by placing the fish in a closed plastic container with water and oxygen for three hours. The fish were continuously fed for two weeks with or without the probiotic supplemented feed. During the two week period the survival rate was observed. Table 5 shows the results.

TABLE 5

Effects of *P. acidilactici* on mortality of gold fish infected with *Ichthypothirius multifilis* and treated with environmental changes as in Table 4.

| Treatment | Total numbers of gold fish | Number of gold fish dead | % of mortality |
|---|---|---|---|
| Control | 20 | 12 | 60% |
| *P. acidilactici* | 20 | 5 | 40% |

Table 5 shows the effect of probiotics on preventing death in biological changed fish—infected with a parasite, and treated with environmental changes as in Table 4.

Dogs suffering from digestive orders chronically-biological changes, and diagnosed as having Inflammatory Bowel Diseases (IBD) symptom, were treated with mixtures of *Pediococcus acidilactici* and *Saccharomyces boulardii* as 1 capsule for body weight (BW) under 5 kg, 2 capsules for BW under 5-15 kg, 3 capsules for BW 15-30 kg, and 4 capsules for BW over 30 kg. The field evaluation were performed at Dakutari Animal Hospital Hiroo Central Hospital (Tokyo, Japan). Table 6 shows the results.

TABLE 6

Effects of probiotics on dogs suffering with Inflammatory Bowel Diseases (IBD)

| Ages | Weight | Sex (M, F, C, S)[1] | Condition prior to feeding probiotics (D, V, C, F, LA)[2] | Symptoms at small intestines (SI), large intestines (LI), other organs | Steroid treatment During probiotic treatment | Days of probiotic treatment | Effects of probiotics |
|---|---|---|---|---|---|---|---|
| 12 | 4.7 | C | ++ D | IBD, LI, Stomatitis | + | 3 | Changed to probiotics only. |

TABLE 6-continued

Effects of probiotics on dogs suffering with Inflammatory Bowel Diseases (IBD)

| Ages | Weight | Sex (M, F, C, S)[1] | Condition prior to feeding probiotics (D, V, C, F, LA)[2] | Symptoms at small intestines (SI), large intestines (LI), other organs | Steroid treatment During probiotic treatment | Days of probiotic treatment | Effects of probiotics |
|---|---|---|---|---|---|---|---|
| 6 | 4.6 | C | ++ D, LA | IBD, LI, Stomatitis +++ | + | 3 | Improving, looks good Changed to probiotics only, Improving, look good |
| 12 | 4.4 | S | ++ D | IBD, LI | + | 7 | Changed to probiotics only, Improving, look good |
| 2 | 3.9 | C | F, Megacolon | IBD, LI | + | 10 | Changed to probiotics only, Improving, look good |
| 2 | 3 | S | + D | IBD, LI | − | 3 | Changed to probiotics only, Improving, look good |

[1]M, male; F, female; C, male, neuter; S: female, spay
[2]D: Diarrhea, O: bad mouth or body odor, V: Vomiting, C: Constipation, F: Flatulence, LA: Loss of Appetite Table 7 shows the beneficial effects of probiotics on dogs with chronic biological change like inflammatory bowel diseases. The results show *P. acidilactici* and *S. boulardii* can be treated together with steroids to alleviate the symptoms While a number of exemplary aspects and embodiments have been discussed above, those of skill in the art will recognize certain modifications, permutations, additions and subcombinations thereof. It is therefore intended that the following appended claims and claims hereafter introduced are interpreted to include all such modifications, permutations, additions and sub-combinations as are within their true spirit and scope. The applicant or applicants have attempted to disclose all the embodiments of the invention that could be reasonably foreseen. There may be unforeseeable insubstantial modifications that remain as equivalents.

I claim:
1. A dry, stable and viable probiotic composition comprising, a blended mixture of at least one biologically pure *Pediococcus acidilactici* probiotic culture and dried tomato powder at a weight ratio of 1:4, and said mixture encapsulated in an effective amount in a gelatin capsule.
2. A process for ameliorating the effects caused by environmental or biological changes in humans or animals comprising the step of feeding the human or animal in need of amelioration of such effects an effective amount of the composition of claim 1.
3. The process of claim 2 wherein the animals are dogs or fish.
4. The process of claim 2 wherein the biological change is Inflammatory Bowel Disease (IBD).

* * * * *